United States Patent
Salisbury et al.

(10) Patent No.: US 8,924,009 B2
(45) Date of Patent: Dec. 30, 2014

(54) HAPTIC DEVICE FOR TELEROBOTIC SURGERY

(75) Inventors: Curt Salisbury, Albuquerque, NM (US);
J. Kenneth Salisbury, Jr., Mountain View, CA (US)

(73) Assignees: The Board of Trustees of the Leland Stanford Junior University, Palo Alto, CA (US); Sandia Corporation, Albuquerque, NM (US)

( * ) Notice: Subject to any disclaimer, the term of this patent is extended or adjusted under 35 U.S.C. 154(b) by 453 days.

(21) Appl. No.: 12/722,332

(22) Filed: Mar. 11, 2010

(65) Prior Publication Data
US 2010/0256815 A1    Oct. 7, 2010

Related U.S. Application Data

(60) Provisional application No. 61/159,350, filed on Mar. 11, 2009.

(51) Int. Cl.
*B25J 13/00*    (2006.01)

(52) U.S. Cl.
USPC ............... 700/245; 606/130; 901/14; 901/40

(58) Field of Classification Search
USPC .......... 606/130, 133; 700/264, 701, 711, 245;
414/7, 5, 6; 901/14, 40; 74/490.04;
345/161; 600/101, 102
See application file for complete search history.

(56) References Cited

U.S. PATENT DOCUMENTS

| | | | |
|---|---|---|---|
| 5,046,375 A | 9/1991 | Salisbury, Jr. et al. | |
| 5,697,256 A | 12/1997 | Matteo | |
| 5,828,197 A * | 10/1998 | Martin et al. | 318/567 |
| 5,952,796 A * | 9/1999 | Colgate et al. | 318/1 |
| 6,046,563 A * | 4/2000 | Moreyra | 318/567 |
| 6,067,077 A * | 5/2000 | Martin et al. | 345/161 |
| 6,255,035 B1 * | 7/2001 | Minter et al. | 430/312 |
| 6,400,352 B1 * | 6/2002 | Bruneau et al. | 345/156 |
| 7,056,123 B2 | 6/2006 | Gregorio et al. | |
| 2007/0106306 A1 * | 5/2007 | Bodduluri et al. | 606/133 |
| 2008/0009771 A1 * | 1/2008 | Perry et al. | 600/587 |
| 2008/0071291 A1 * | 3/2008 | Duval et al. | 606/130 |
| 2009/0163929 A1 * | 6/2009 | Yeung et al. | 606/130 |
| 2010/0170361 A1 * | 7/2010 | Bennett et al. | 74/490.04 |
| 2010/0204713 A1 * | 8/2010 | Ruiz Morales | 606/130 |
| 2010/0228264 A1 * | 9/2010 | Robinson et al. | 606/130 |

OTHER PUBLICATIONS

Salisbury et al.; A microsurgery-specific haptic device for telerobotic medical treatment; American Nuclear Society; 2nd Int. Joint Topical Mtg. on Emergency Preparedness and Response and Reobotic and Romote Systems 2008; Albuquerque, NM; pp. 404-410; Mar. 9-12, 2008.

* cited by examiner

*Primary Examiner* — Ronnie Mancho
(74) *Attorney, Agent, or Firm* — Shay Glenn LLP (57) ABSTRACT

A haptic device for telerobotic surgery, including a base; a linkage system having first and second linkage members coupled to the base; a motor that provides a motor force; a transmission including first and second driving pulleys arranged such that their faces form an angle and their axes form a plane, first and second idler pulleys offset from the plane and arranged between the first and second driving pulleys such that their axes divide the angle between the first and second driving pulleys, and a cable that traverses the first and second driving pulleys and the set of idler pulleys and transfers the motor force to the linkage system; an end effector coupled to distal ends of the first and second linkage members and maneuverable relative to the base; and a controller that modulates the motor force to simulate a body part at a point portion of the end effector.

29 Claims, 6 Drawing Sheets

HAPTIC DEVICE FOR TELEROBOTIC SURGERY

CROSS-REFERENCE TO RELATED APPLICATIONS

This application claims the benefit of U.S. Provisional Application No. 61/159,350, filed 11 Mar. 2009, which is incorporated in its entirety by this reference.

STATEMENT OF GOVERNMENT INTEREST

The United States Government has rights in this invention pursuant to Contract No. DE-AC04-94AL85000 between the United States Department of Energy and Sandia Corporation, for the operation of the Sandia National Laboratories.

TECHNICAL FIELD

This invention relates generally to the haptic device field, and more specifically to an improved haptic device for telerobotic surgery.

BACKGROUND

Telerobotics, in which a robot is controlled from a distance, is an area of robotics that is useful in many applications, such as in surgery. Telerobotic systems consist of a master robot and a slave robot. In surgery, the surgeon directly controls the master robot, which results in motion of the slave robot at the patient. The master robot and slave robot, which are physically separated, may be close to each other (e.g., in the same room) or remote from each other (e.g., on different continents).

In replicating the environment found in a conventional procedure, the user interface of the master robot ideally accommodates the desired motions of the surgeon (i.e., includes sufficient degrees of freedom), and mechanically simulates the feel and touch of the actual environment (i.e., provides haptic feedback). To provide haptic cues, actuators in the slave robot typically generate an opposing force against a user-manipulated item such as a grasper or stylus. These forces are transmitted from the actuators to the stylus through a haptic device transmission. Haptic device transmissions ideally have minimal friction, minimal inertia, minimal or no cogging and grinding, high stiffness, and no backlash. Haptic devices have historically included cable and pulley transmissions, which most effectively address theses requirements.

However, simply providing haptic feedback is not enough during certain procedures, such as those requiring high bandwidth haptics, in which the tactile feedback to the user is updated at a high frequency. For example, haptics with low inertia and high bandwidth are advantageous in microsurgery, which typically involves procedures performed by hand under a microscope. This is due in part to the low mass and low inertia of microsurgical tools, and in part to the subtle, high frequency haptic cues used for navigation. As one illustrative example, a stapedotomy (during which the surgeon drills a hole in the stapes footplate in the ear for the insertion of a prosthesis) is ideally performed with a haptic device having high bandwidth and low inertia. In this procedure, care must be taken to avoid perforating the cochlear membrane behind the stapes, making a stapedotomy analogous to drilling through an eggshell without puncturing the membrane inside the egg. The haptic cue that a surgeon monitors to avoid damaging the cochlear membrane is the sudden drop in mechanical resistance on the drill during penetration of the bone. Low bandwidth haptic devices are, by definition, slower to respond and would potentially mask this cue and possibly increase the incidence of complications if used as telerobotic masters.

Thus, there is a need in the haptics field to create an improved haptic device for surgery with lower effective inertia and higher bandwidth, which may also be adapted to use in a wider range of types of robotic surgery and simulation. This invention provides such an improved haptic device for surgery.

DESCRIPTION OF THE PREFERRED EMBODIMENTS

The following description of preferred embodiments of the invention is not intended to limit the invention to these preferred embodiments, but rather to enable any person skilled in the art to make and use this invention.

Figure 1:
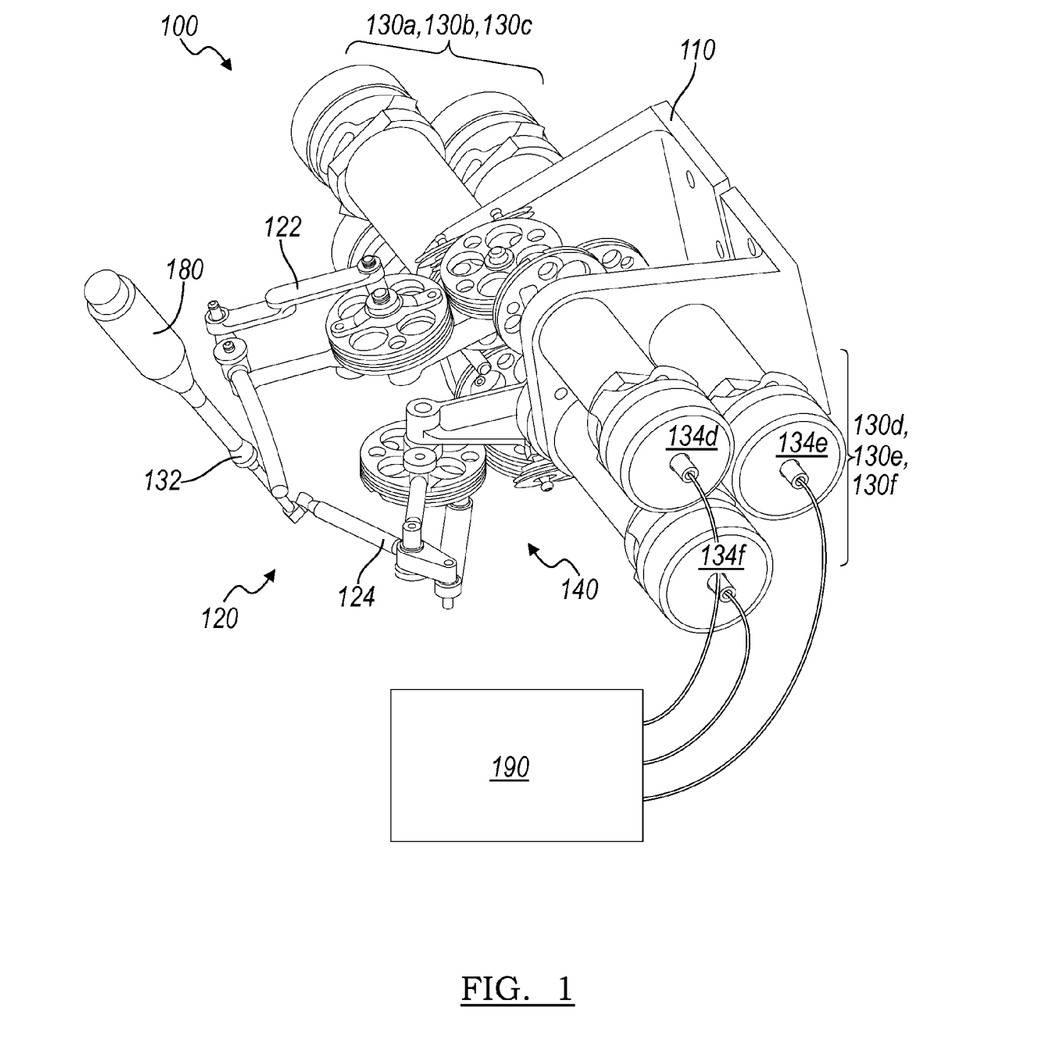
FIG. 1 is a perspective view of the preferred embodiment of the haptic device.

As shown in FIG. 1, the haptic device 100 of the preferred embodiment includes a base 110; a linkage system 120 including a first linkage member 122 and a second linkage member 124; at least one motor 130 that provides a motor force to drive the linkage system 120; a transmission 140 that transfers the motor force to the linkage system 120 and includes a set of driving pulleys 150, a set of idler pulleys 170, and a cable 146 that traverses the set of driving pulleys 150 and the set of idler pulleys 170; an end effector 180 coupled to the first and second linkage members and maneuverable relative to the base no; and a controller 190 that modulates the motor force to simulate a body part at the end effector. The haptic device 100 preferably has six degrees of freedom and provides haptic feedback by applying force, vibration, and/or other suitable mechanical stimulation to a surgeon or other user, which assists in simulation of body tissue or any suitable virtual object. The user interface feel of the haptic device 100 preferably resembles a light surgical tool, with similar mass and inertial properties. The haptic device 100 preferably provides a haptic environment with low effective inertia and high bandwidth suitable for us during telerobotic surgery, particularly microsurgery in which surgery is performed on a microscopic scale. During use in telerobotic surgery, the haptic device 100 is preferably a "slave robot" through which a user controls a "master robot" that performs motions resulting from manipulations of the slave robot by the user. However, the haptic device 100 may be used during other kinds of robotic surgery, other telerobotic applications, simulation, and/or any suitable haptics application.

1. The Base, Linkage System, and Motors

The base 110 of the haptic device functions to form a ground member for the linkage system 120 and to provide support for the haptic device on a surface. As shown in FIG. 1, the base 110 preferably includes two walls that ground and support the motors and linkage system 120, preferably grounding the first linkage member 122 on one wall, and grounding the second linkage member 124 on another wall. However, the base 110 may alternatively include a single wall or surface that grounds both linkage members. The base no is preferably adapted to mount to a workspace such as a table, desk, or wall, such as with brackets, screws, adhesives, or any suitable fasteners. Alternatively, the base 110 may include magnets or a heavy weight to secure the base to a workspace and may allow the haptic device to be operable in a broader range of environments, which may be particularly useful for some telerobotic applications. The base may be made of one piece or multiple pieces that are attached together and/or to the workspace.

Figure 4:
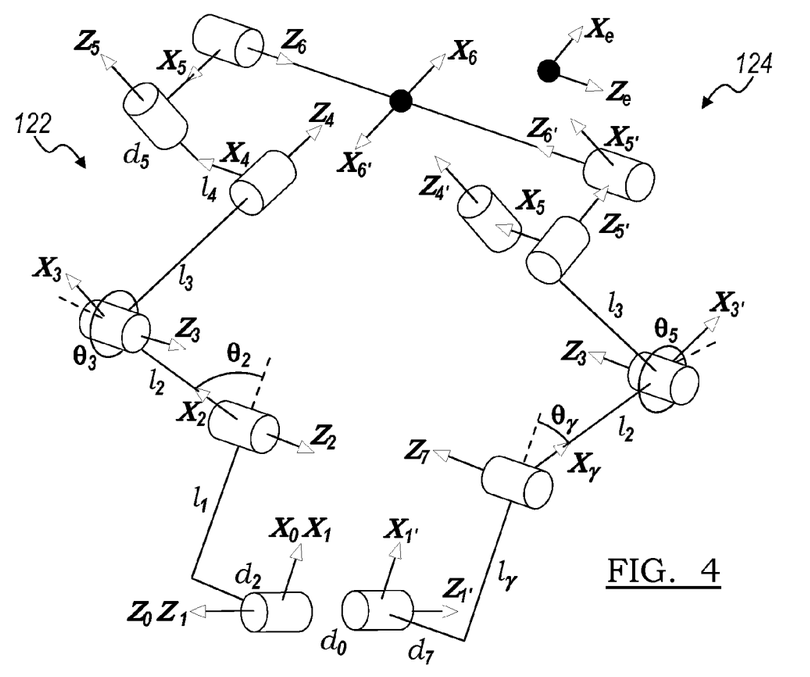
FIG. 4 is a kinematic model of joined linkage members of the preferred embodiment of the haptic device.

The linkage system 120 of the preferred embodiment functions to allow the end effector 180 to be maneuvered relative to the base 110. The linkage system preferably includes a first linkage member 122 and a second linkage member 124 that are coupled to the base 110. The first and second linkage members are preferably similar, and more preferably mirror versions of each other, but may alternatively be different structures of different designs. Each of the linkage members preferably has three degrees of freedom that are adapted to be actuated. As shown in FIG. 4, each linkage member is preferably a serial jointed, three revolute (RRR) manipulator. However, each linkage member may be any suitable kind of linkage. Such robot kinematics are familiar to those skilled in the art. At least some segments or portions of the linkage members are preferably hollow or provide a passageway for the cable of the transmission to route to particular joints of the linkage members. In a preferred embodiment, which may be particularly designed for telerobotic haptic surgery, the workspace facilitated by the linkage system 120 is preferably small enough to avoid singularities common to RRR mechanisms (wrist lock, elbow lock, and head lock) and to not disrupt function of the haptic device.

The motors 130 of the preferred embodiment functions to provide a motor force that is used to drive or actuate the linkage system 120 to provide haptic feedback to the user. The haptic device 100 preferably includes at least one motor per degree of freedom. In the preferred embodiment, the haptic device includes seven motors, including six linkage motors 130a-130f and one distal motor 132 within the end effector. The motors preferably have low rotor inertia and low friction (in particular, low stiction) to help accurately simulate the feel of a light surgical tool. Lower rotor inertia results in a lower effective joint inertia, since the effective inertia of each joint in the haptic device is proportional to rotor inertia. Similarly, lower motor stiction results in a lower effective joint stiction, since effective joint stiction of each joint in the haptic device is proportional to motor stiction. Both effective joint inertia and effective joint stiction are also functions of mechanical advantage at each joint, which is dependent on the torque provided by the motor and the amount the torque that each joint must provide to result in a desired maximum force applied to and felt by the user. As shown in FIG. 1, the linkage motors 130 are preferably mounted on the base 110, such that the linkage motors are physically grounded to minimize their effective tool inertia, but the linkage motors 130 may alternatively be located in any suitable location throughout the device. As shown in FIG. 1, three linkage motors 130a, 130b, and 130c are preferably coupled to the first linkage member 122 such that each of these linkage motors drives one of three degrees of freedom of the first linkage member. Three linkage motors 130d, 130e, and 130f are preferably similarly coupled to the second linkage member such that each of these linkage motor drives one of three degrees of freedom of the second linkage member. As kinematic analysis will show, the combined linkage system of the two linkage members, joined by the end effector, has five fully actuated degrees of freedom. The distal motor 132 in the end effector preferably actuates a sixth degree of freedom of the haptic device, thereby eliminating a planar singularity in the kinematic analysis that exists without the distal motor. In one specific embodiment, the linkage motors 130 are Maxon RE-25 motors and the distal motor 132 is a Maxon RE-13 motor.

Each of the motors is preferably paired with an encoder 134 that monitors the position and/or velocity of the motor. To better simulate the environment of the master robot, the haptic device 100 preferably has a task space resolution similar to that of the actual environment. In order to obtain a high effective resolution, the encoders 134 are preferably coupled in direct drive with the motors and have a resolution on the order of 10,000 cycles per revolution, since a lower mechanical advantage preferably has encoders with correspondingly higher resolution to compensate and result in a high effective resolution. However, to increase effective resolution of an encoder 134 with an inherently lower resolution, the gain from the motor to the encoder may alternatively be increased with a suitable mechanical advantage. Alternatively, the motor to encoder mechanical advantage may be lower and the encoders may have lower resolution, such that the haptic device has any suitable level of resolution. The encoders 134 may be relatively inexpensive LED encoders having a high resolution. In a specific embodiment, the LED encoders include encoder wheels with lines so narrow that the resultant analog signal resembles a sine wave, and may be read by using an interpolation method of quantization thresholding to select values of the sine wave to drive a square wave encoder output signal. This interpolation method preferably improves LED encoder resolution by as much as 20 times. Alternatively, the encoders 134 may be laser encoders or any suitable kind of encoder, and may have inherently relatively high resolution and/or be read in the conventional direct manner.

2. The Transmission

The transmission 140 of the preferred embodiment functions to transfer motor force to the linkage system 120. The transmission 140 is preferably a cable drive transmission that includes four instances of a group of: a set of driving pulleys 150, a set of idler pulleys 170, and a cable 146 that traverses the set of driving pulleys 150 and the set of idler pulleys 170 and is coupled to the motor force and the linkage system 120. The four instances of sets of driving pulleys, idler pulleys, and cable are preferably similar, but may alternatively be different. Two instances are preferably used to drive the first linkage member, and two instances are preferably used to drive the second linkage member. The cable drive transmission is preferably compact, designed to minimize the amount of free length of cable in the transmission (the total cable length that is not engaged with a driving pulley, an idler pulley, or other driving or routing element), thereby increasing bandwidth of the haptic device. A compact transmission also reduces the overall size of the haptic device and improves portability.

Figure 5:
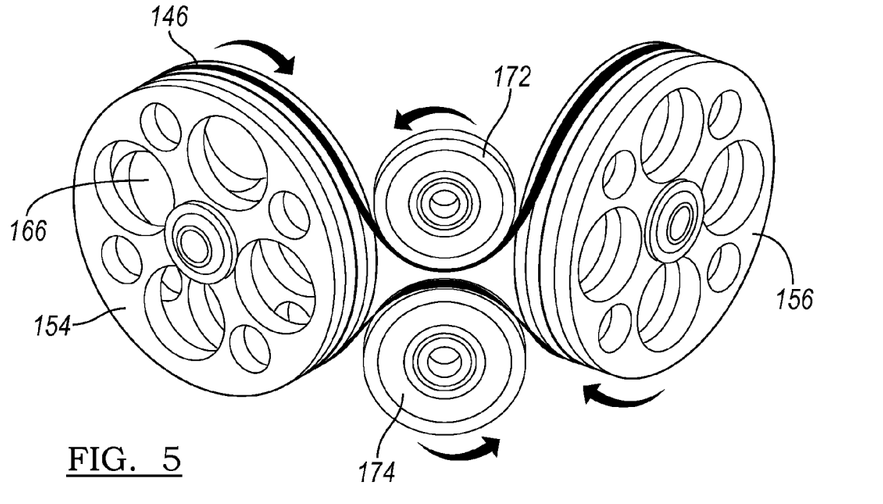
FIG. 5 is a schematic of one instance of the pulley set groups including driving pulleys and idler pulleys for driving one degree of freedom in the preferred embodiment of the haptic device.
Figure 6:
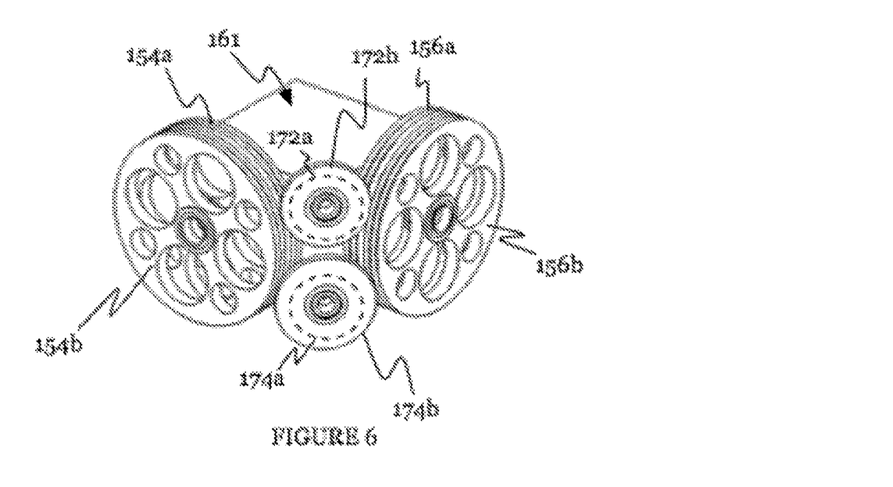
FIG. 6 is a schematic of two adjacent instances of the pulley set groups including driving pulleys and idler pulleys for driving two degrees of freedom in the preferred embodiment of the haptic device.
Figure 7:
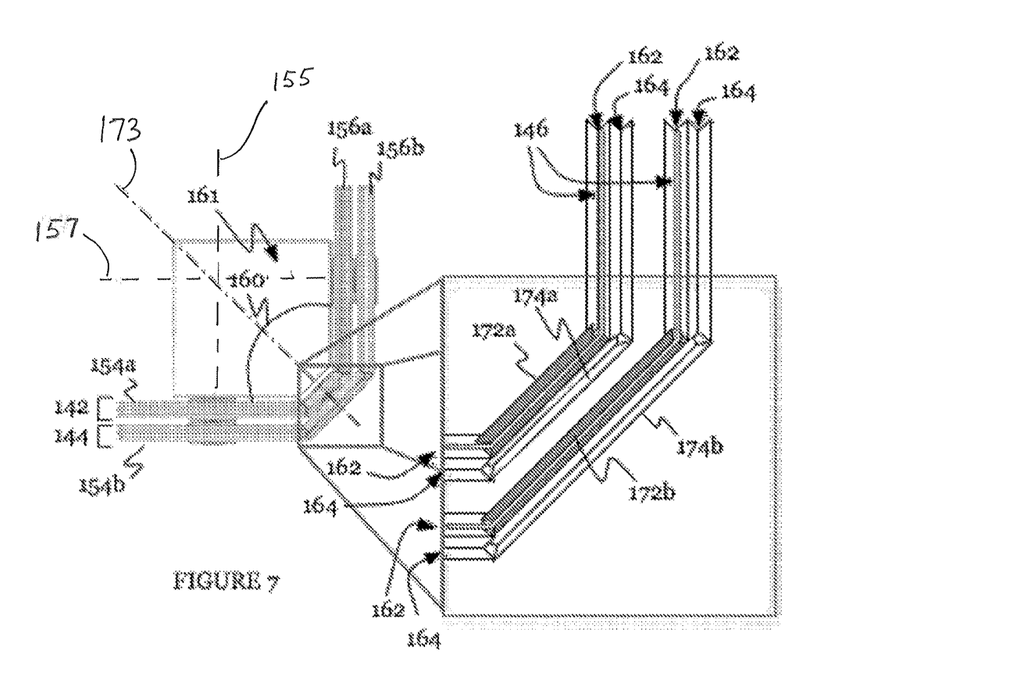
FIG. 7 is a schematic of a portion of the transmission in the preferred embodiment of the haptic device.

In each instance of pulley set groups, as shown in FIGS. 5-7, the set of driving pulleys 150 preferably includes a first driving pulley 154 and a second driving pulley 156 that are arranged such that their faces form an angle 160 and their axes of rotation 155 and 157, respectively, form a plane 161. As best shown in FIG. 7, the angle 160 is preferably a right angle, but may alternatively form any suitable angle. Each of the first and second driving pulleys 154 and 156 is preferably double grooved, such that each preferably includes a pair of circumferential pulley grooves. The pair of circumferential pulley grooves preferably includes a forward groove 162 that accommodates a forward cable path for the cable traversing towards the linkage system 120, and a reverse groove 164 that accommodates a reverse cable path traversing away from the linkage system 120. The driving pulleys are preferably constructed of a lightweight rigid material such as aluminum, but may alternatively be constructed of any suitable material. The driving pulleys are preferably relatively large, to be able to transmit a given torque to a linkage member joint with smaller changes in cable tension, which results in overall greater stiffness and consequently higher bandwidth for the haptic device. The driving pulleys preferably have holes cut into their bodies to remove mass, which allows the driving pulleys to be larger without significantly increasing device inertia.

Figure 3:
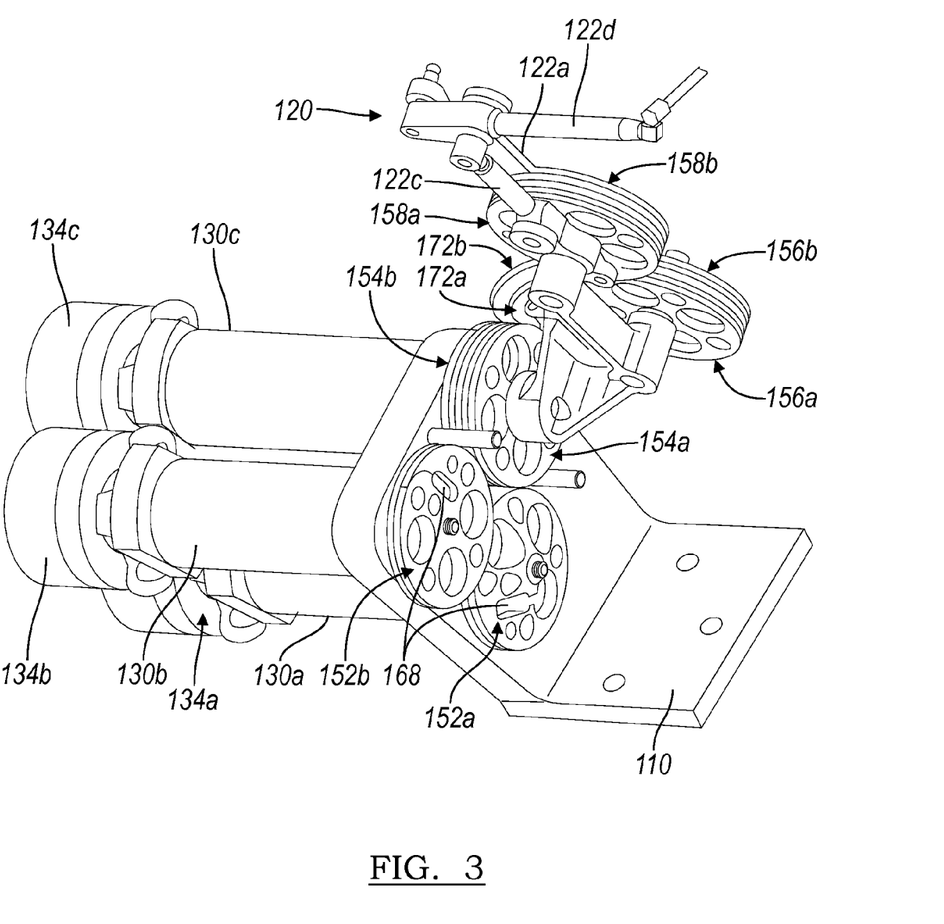

As best shown in FIG. 3, the set of driving pulleys preferably further includes a third and a fourth driving pulleys, and may further include additional driving pulleys, although in some embodiments the set of driving pulleys may consist of only the first and second driving pulleys. A third driving pulley 152 preferably is coupled to the motor and includes a recess 168 in the body of the third driving pulley 152 that facilitates coupling to one or both ends of the cable 146, thereby coupling the cable to the motor force. As shown in FIG. 3, the recess 168 is preferably in a face of the pulley and is adapted to receive a stop (e.g., a block end) of the cable, but the recess 168 may alternatively be located in any suitable location on the third pulley. Alternatively, the third driving pulley 152 may include a fastener such as a clasp, be adapted to adhere to the cable end such as by adhesive, welding, or brazing, or be adapted to couple to the cable end in any suitable manner. A fourth driving pulley 158 is preferably adjacent to the second driving pulley 156 and may be located on a linkage member, such that the cable 146 traverses the fourth driving pulley 158.

In each instance of pulley set groups, as shown in FIG. 5, the set of idler pulleys 170 preferably includes a first idler pulley 172 and a second idler pulley 174. The first and second idler pulleys are preferably offset (i.e. spaced apart) from the plane 161 that is formed by the axes of rotation 155 and 157 of the first and second driving pulleys 154 and 156. As shown in FIG. 5, the first and second idler pulleys 172 and 174 are preferably offset or spaced apart from the plane 161 in opposite directions such that they are on opposite sides of plane 161 from one another. The first and second idler pulleys 172 and 174 are preferably similarly sized, offset or spaced apart from the plane by equal distances, and aligned with each other across the plane, such that the combination of the first and second driving pulleys and the first and second idler pulleys is substantially bilaterally symmetrical across the plane 161. However, the first and second idler pulleys may alternatively be offset by unequal distances and/or be different sizes. As shown in FIG. 7, the first and second idler pulleys 172 and 174 are preferably arranged between the first and second driving pulleys 154 and 156 such that a projection 173 of the axis of each of the first and second idler pulleys onto plane 161 divides the angle 160 formed by the first and second driving pulleys, and more preferably substantially bisects the angle, to help guide the cable around the angle. Since the angle 160 formed by the first and second driving pulleys is preferably a right angle, the first and second idler pulleys 172 and 174 are preferably arranged at a 45 degrees angle relative to the first and second driving pulleys 154 and 156. As shown in FIG. 5, the first and second idler pulleys 172 and 174 are preferably arranged relative to the first and second driving pulleys 154 and 156 such that the first and second idler pulleys 172 and 174 share a tangent line with one or both of the first and second driving pulleys, making the transmission further compact. One of the first and second idler pulleys is preferably aligned with the forward grooves of the first and second driving pulleys, and the other idler pulley is preferably aligned with the reverse grooves of the first and second driving pulleys. To accommodate both the alignment and the tangential arrangement, one of the idler pulleys is preferably slightly larger than the other idler pulley. For example, as best shown in FIG. 7, idler pulley 172a may be aligned with the "inside" forward grooves 162 of the driving pulleys 154a and 156a, and idler pulley 174a may be aligned with the "outside" reverse grooves 164 of the driving pulleys 154a and 156a. To maintain tangential alignment, as shown in FIG. 3, idler pulley 172b is preferably slightly larger than idler pulley 172a. One advantage of the tangential arrangement of driving pulleys and idler pulleys is the minimized space that the cable 146 must span when traversing between a driving pulley and an idler pulley, thereby increasing bandwidth of the haptic device 100 and resulting in an improved haptic interface with more frequently updated haptic cues to the user. Another advantage of this arrangement is less cable deformation as the cable traverses between a driving pulley and an idler pulley, resulting in less friction as the cable moves and contributing to a lower effective inertia and lighter feel for the user.

The set of idler pulleys 170 may further include additional idler pulleys in suitable locations to help orient the cable. The idler pulleys 172 and 174 are preferably made of a lightweight material similar to that of the driving pulley material, but may or may not have holes. The idler pulleys are preferably smaller than the driving pulleys, and more preferably have a diameter approximately half or less than half of the diameter of the driving pulleys, such that the first and second idler pulleys, when arranged in the transmission, do not extend beyond the boundaries of the first and second driving pulleys.

In each instance of pulley set groups, the cable 146 is preferably braided wire rope, which provides more flexibility for routing around the pulleys in the transmission. The specific kind of braiding and diameter of the wire rope may depend on the diameter of the driving and idler pulleys, the cable bend radius required to traverse the pulleys, the width of pulley grooves on the driving pulleys, the specific arrangement of the driving and idler pulleys, and/or any other suitable characteristic of the transmission. However, any suitable cable, string, or other flexible lengths may be used in the transmission. The cable 146 is preferably one continuous length, but may alternatively be separate lengths whose ends are fastened to and traverse the driving and/or idler pulleys.

As shown in FIG. 7, a second instance of the pulley set groups (denoted with "b") is preferably stacked adjacent to a first instance (denoted with "a") of the pulley set groups to drive the first linkage member. The sets of driving and idler pulleys of the first instance preferably form an inner pulley layer 142 that drives one degree of freedom of the first linkage member, and the sets of driving and idler pulleys of the second instance preferably form an outer pulley layer 144 that drives another degree of freedom of the first linkage member. The inner pulley layer 142 and the outer pulley layer 144 are preferably parallel such that the driving pulleys 154 and 156 of both pulley layers form substantially equal angles. Similarly, third and fourth instances of the pulley set groups are preferably stacked adjacent to each other to drive two degrees of freedom of the second linkage member.

Figure 2:
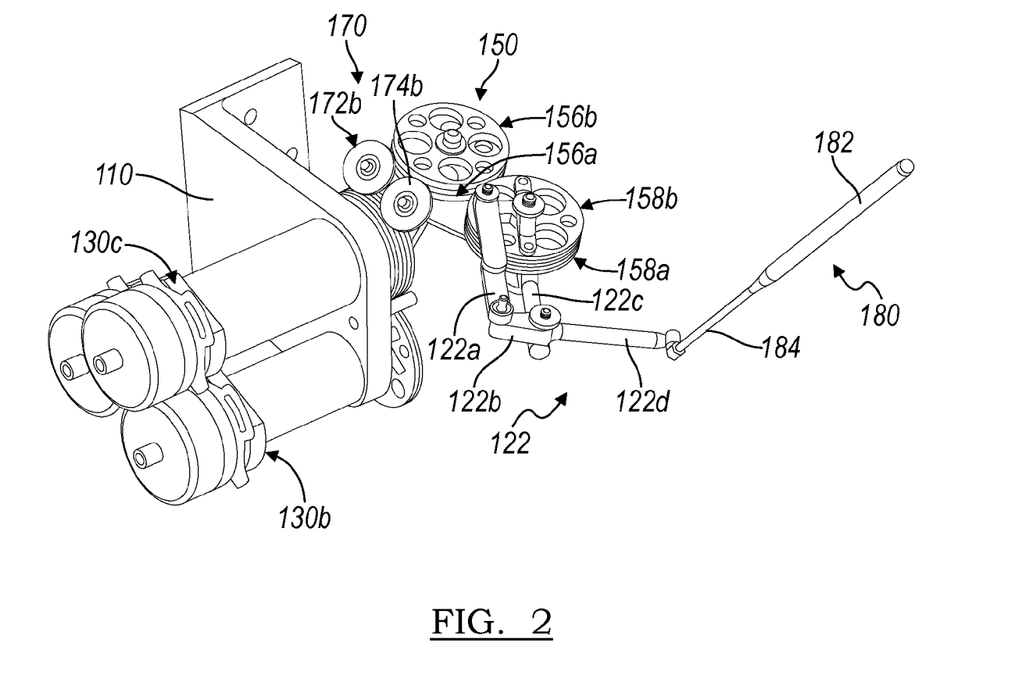
FIGS. 2 and 3 are front and underside perspective views, respectively, of a portion of the preferred embodiment of the haptic device.

As shown in FIGS. 2 and 3, to drive a first degree of freedom of the first linkage member 122 in which the linkage segment 122d axially rotates relative to the linkage segment 122b, a first cable preferably traverses the driving and idler pulleys in the forward cable path in the following order: (1) originates from and routes within the forward groove of the driving pulley 152a that is coupled to the shaft of motor 130a in direct drive, (2) routes within forward groove around driving pulley 154a, (3) routes around idler pulley 172a aligned with the forward grooves of the driving pulleys 154a and 156a, respectively, (4) routes within forward groove around driving pulley 156a, (5) routes within forward groove around driving pulley 158a, and (6) routes through linkage segment 122C of the first linkage member to the joint between linkage segments 122b and 122C. The cable 146 preferably traverses the driving and idler pulleys in reverse order in the reverse cable path in the following order: (7) routes through the linkage segment 122C, (8) routes within reverse groove around driving pulley 158a, (9) routes within reverse groove around driving pulley 156a, (10) routes around the idler pulley 174a, (11) routes within reverse groove around driving pulley 154a, (12) routes within reverse groove around the driving pulley 152a, and (13) terminates in driving pulley 152a. Furthermore, as shown in FIGS. 2 and 3, to drive a second degree of freedom of the first linkage member 122 in which linkage segment 122b rotates relative to the linkage segment 122a, a second cable preferably traverses the driving and idler pulleys in the forward cable path in the following order: (1') originates from and routes within the forward groove of driving pulley 152b that is coupled to the shaft of motor 130b in direct drive, (2') routes within forward groove around driving pulley 154b, (3') routes around idler pulley 172b aligned with forward grooves of driving pulleys 154b and 156b, (4') routes within forward groove around driving pulley 156b, (5') routes within forward groove around driving pulley 158b, and (6') routes through linkage segment 122a to the joint between linkage segments 122a and 122b. The cable preferably traverses the driving and idler pulleys in the reverse cable path in the following order: (7') routes through linkage segment 122a, (8') routes within reverse groove of driving pulley 158b, (9') routes within reverse groove of driving pulley 156b, (10') routes around idler pulley 174b, (11') routes within reverse groove of driving pulley 154b, (12') routes within reverse groove of driving pulley 152b, and (13') terminates in driving pulley 152b. To drive a third degree of freedom of the first linkage member, motor 130c preferably rotates the first linkage member 122 in direct drive. The first, second, and third degrees of freedom of the second linkage member 124 are preferably driven in a similar manner as those of the first linkage member. Variations of the cable paths include every combination and permutation of the driving and idler pulleys. Although in FIG. 7 the forward cable path is the inner pulley track 142 and the reverse cable path is the outer pulley track 144, in some embodiments the forward cable path may be the outer pulley track 144 and the reverse cable path may be in the inner pulley track 142. The forward cable path may include either of the first or second idler pulleys, and the reverse cable path may include either of the first and second idler pulleys. Furthermore, the forward and/or reverse cable paths may include fewer than all of the driving and idler pulleys present in the transmission.

3. The End Effector and Controller

The end effector 180 of the preferred embodiment functions as the piece manipulated by the user. As shown in FIG. 2, the end effector 180 preferably includes a handle portion and a point portion opposite the handle portion. The handle portion 182 of the end effector 180 is preferably adapted to be held or manipulated by the user, and is preferably a stylus, grasper, or other suitable instrument that simulates operation of a surgical tool or instrument such as a scalpel, drill, clamp, or any suitable instrument that may be on the master robot. The point portion 184 is the portion at which the effective forces transferred through the transmission and linkage system 120 most closely resemble the simulated environment (e.g., the feel of a body part during surgery). The end effector 180 is preferably coupled to the distal ends of the first and second linkage members 122 and 124 and is adapted to maneuver relative to the base 110. As shown in FIG. 1, the distal ends of the first and second linkage members 122 and 124 are preferably coupled in the point portion of the end effector, preferably separated by less than about 25% of the length of the effector. In one specific embodiment, the distal ends of the first and second linkage members 122 and 124 are separated on the end effector by approximately one inch. The connection or joining of the linkage members to the same end of the end effector 180 increases workspace and minimizes device interference with the user's hand, while maintaining the ability to render to the user an amount of torque that is consistent with the torques observed during surgery. Alternatively, the first and second linkage members 122 and 124 may be attached to opposite ends of the effector (one linkage member coupled to the handle portion and the other linkage member coupled to the point portion), which increases the amount of torque that the device can render to the user, which may be desired for different kinds of procedures or simulations. By joining the distal ends of the linkage members, the end effector 180 connects the serial linkage members 122 and 124 in parallel. Serial mechanisms exhibit exceptional range of motion with minimal workspace intrusion, and parallel mechanisms exhibit exceptional stiffness and low inertia for a given desired device force output. By combining serial mechanisms in a parallel structure, the hybrid kinematic design of the haptic device provides an optimal balance of high stiffness, low inertia, high range of motion, and low workspace intrusion.

Figure 8:
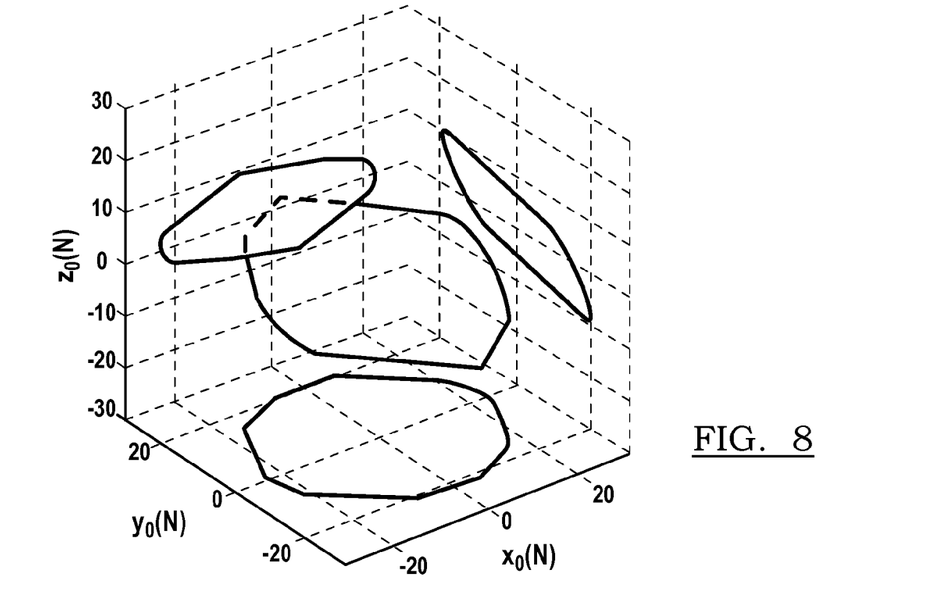
FIG. 8 is a plot of the maximum force output of an embodiment of the haptic device.
Figure 9:
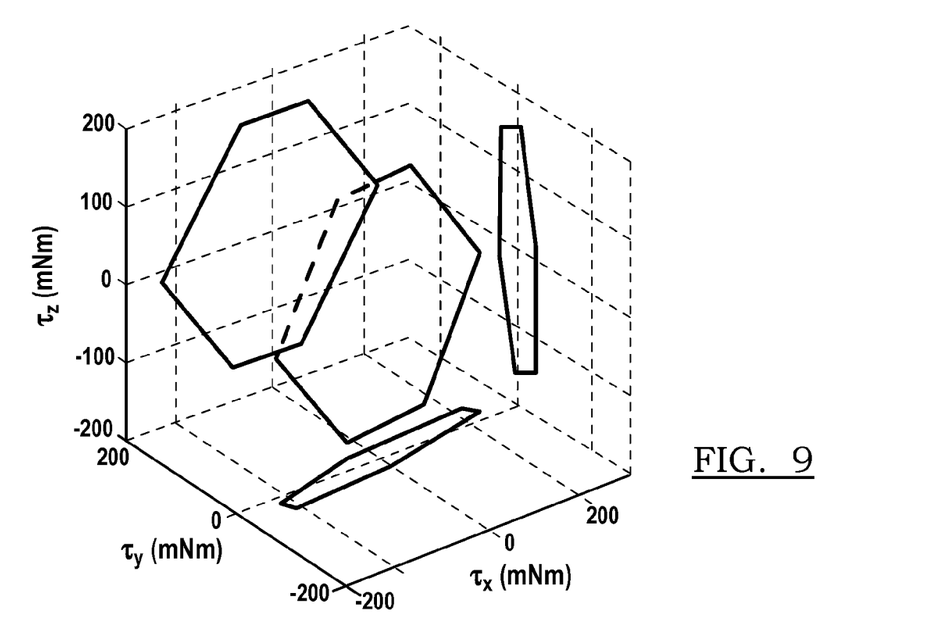
FIG. 9 is a plot of the maximum torque output of an embodiment of the haptic device.

The controller 190 functions to modulate the motor force of each motor to simulate a virtual object at the point portion of the end effector. The controller 190 preferably takes into account the force output of the haptic device at the end effector, and may analyze the torque felt by the user maneuvering the end effector with a torque array resulting from kinematic analysis of the linkage system 120 and end effector. Suitable analyses and control mechanisms are known to one skilled in the art. The controller preferably modulates the motor force such that the haptic device preferably provides an amount of force and torque, as shown in FIGS. 8 and 9 respectively, in all directions that are appropriate and sufficient for the purposes of microsurgery and other simulates on a similar scale.

As a person skilled in the art will recognize from the previous detailed description and from the figures and claims, modifications and changes can be made to the preferred embodiments of the invention without departing from the scope of this invention defined in the following claims.

We claim:
1. A drive system for a linkage system, comprising:
a set of driving pulleys including a first driving pulley and a second driving pulley, the first driving pulley having a first driving axis of rotation and the second driving pulley having a second driving axis of rotation, wherein the first driving axis of rotation is angularly displaced from the first driving axis of rotation within a plane, thereby defining an angle between the first and second driving pulleys;

a set of idler pulleys arranged between the first and second driving pulleys, the set of idler pulleys including a first idler pulley having a first idler axis of rotation and a second idler pulley having a second idler axis of rotation, wherein each of the first and second idler axes of rotation is substantially parallel to the plane and wherein a projection of at least one of the first and second idler axes onto the plane substantially bisects the angle between the first and second driving pulleys, and;

a motor configured to provide a motor force; and a cable that traverses the set of driving pulleys and the set of idler pulleys, wherein the cable is configured to couple to the motor force and to the linkage system such that the cable transfers the motor force to the linkage system.

2. The drive system of claim 1, wherein the angle between the first and second driving pulleys is approximately a right angle.

3. The drive system of claim 1, wherein each of the first and second idler pulleys share a tangent line with at least one of the first and second driving pulleys.

4. The drive system of claim 1, wherein the first and second idler axes of rotation are spaced apart from the plane on opposite sides of the plane from one another.

5. The drive system of claim 1, wherein each of the first and second driving pulleys includes a pair of parallel circumferential pulley grooves, wherein the pair of circumferential pulley grooves includes a forward groove that accommodates a forward cable path for the cable traversing towards the linkage system, and a reverse groove that accommodates a reverse cable path traversing away from the linkage system.

6. The drive system of claim 5, wherein the cable traverses the forward groove of the first driving pulley followed by the first idler pulley, followed by the forward groove of the second driving pulley.

7. The drive system of claim 6, wherein the cable traverses the reverse groove of the second driving pulley followed by the second idler pulley, followed by the reverse groove of the first driving pulley.

8. The drive system of claim 1, wherein the set of driving pulleys further comprises a third driving pulley coupled to the motor, wherein an end of the cable is coupled to the third driving pulley, thereby coupling the cable to the motor force.

9. The drive system of claim 8, wherein the set of driving pulleys further comprises a fourth driving pulley, adjacent to the second driving pulley, wherein the cable traverses the fourth driving pulley.

10. The drive system of claim 1, further comprising:
a second set of driving pulleys rotatable independently of the first set of driving pulleys;
a second set of idler pulleys; and
a second cable traversing the second set of driving pulleys and the second set of idler pulleys;
wherein the first set of driving pulleys and the first set of idler pulleys form an inner pulley layer, and the second set of driving pulleys and the second set of idler pulleys form an outer pulley layer arranged adjacent to the inner pulley layer.

11. The drive system of claim 10, wherein the second set of driving pulleys includes a fifth driving pulley and a sixth driving pulley, wherein the fifth and sixth driving pulleys are arranged to form a second angle between the fifth and sixth driving pulleys that is substantially equal to the first angle between the first and second driving pulleys.

12. The drive system of claim 10, wherein the second cable is coupled to a second motor and configured to couple to the linkage system, wherein the first cable drives a first degree of freedom of the linkage system, and the second cable drives a second degree of freedom of the linkage system.

13. A haptic device for telerobotic surgery, comprising:
a base;
a linkage system including a first linkage member and a second linkage member coupled to the base, wherein each of the first and second linkage members has a distal end;
a motor configured to provide a motor force to drive the linkage system;
a transmission that transfers the motor force to the linkage system, including:
a set of driving pulleys including a first driving pulley and a second driving pulley, the first driving pulley having a first driving axis of rotation and the second driving pulley having a second driving axis of rotation, wherein the first driving axis of rotation is angularly displaced from the first driving axis of rotation within a plane, thereby defining an angle between the first and second driving pulleys;
a set of idler pulleys arranged between the first and second driving pulleys, the set of idler pulleys including a first idler pulley having a first idler axis of rotation and a second idler pulley having a second idler axis of rotation, wherein each of the first and second idler axes of rotation is substantially parallel to the plane; and
a cable that traverses the set of driving pulleys and the set of idler pulleys, wherein the cable is configured to couple to the motor force and to the linkage system such that the cable transfers the motor force to the linkage system;
an end effector coupled to the distal ends of the first and second linkage members and maneuverable relative to the base, wherein the end effector has comprises a handle portion and a point portion distal to the handle portion; and
a controller that is configured to modulate the motor force to simulate an object at the point portion of the end effector.

14. The haptic device of claim 13, wherein each of the first and second idler pulleys shares a tangent line with at least one of the first and second driving pulleys.

15. The haptic device of claim 13, wherein each of the first and second driving pulleys includes a forward groove that accommodates a forward cable path for the cable traversing towards the linkage system, and a reverse groove that accommodates a reverse cable path traversing away from the linkage system, wherein the cable traverses the forward groove of the first driving pulley followed by the first idler pulley, followed by the forward groove of the second driving pulley.

16. The haptic device of claim 15, wherein the cable traverses the reverse groove of the second driving pulley followed by the second idler pulley, followed by the reverse groove of the first driving pulley.

17. The haptic device of claim 13, further comprising:
a second set of driving pulleys rotatable independently of the first set of driving pulleys;
a second set of idler pulleys; and
a second cable traversing the second set of driving pulleys and the second set of idler pulleys;
wherein the first set of driving pulleys and the first set of idler pulleys form an inner pulley layer, and the second set of driving pulleys and the second set of idler pulleys form an outer pulley layer arranged adjacent to the inner pulley layer.

18. The haptic device of claim 17, wherein the second cable is coupled to a second motor configured to provide a second motor force and coupled to the linkage system, wherein the first cable and first motor force drive a first degree of freedom of the first linkage member, and the second cable and second motor force drive a second degree of freedom of the first linkage member.

19. The haptic device of claim 18, further comprising a proximal motor, coupled to a proximal end of the first linkage member, that drives a third degree of freedom of the first linkage member.

20. The haptic device of claim 13, wherein the distal ends of the first and second linkage mechanisms are coupled to the point portion of the end effector.

21. The haptic device of claim 13, further comprising a third motor configured to provide a third motor force and a second transmission coupled to the second linkage member, wherein the second transmission includes:
 a third set of driving pulleys;
 a third set of idler pulleys; and
 a third cable that traverses the third set of driving pulleys and the third set of idler pulleys;
 wherein the third cable is coupled to the third motor and coupled to the second linkage member, such that the third cable transfers the third motor force to drive a first degree of freedom of the second linkage member.

22. The haptic device of claim 21, further comprising a fourth motor configured to provide a fourth motor force, wherein the second transmission further includes:
 a fourth set of driving pulleys rotatable independently of the third set of driving pulleys;
 a fourth set of idler pulleys; and
 a fourth cable that traverses the fourth set of driving pulleys and the fourth set of idler pulleys;
 wherein the fourth cable is coupled to the fourth motor and coupled to the second linkage member, such that the fourth cable transfers the fourth motor force to drive a second degree of freedom of the second linkage member; and
 wherein the third set of driving pulleys and the first set of idler pulleys form an inner pulley layer, and the fourth set of driving pulleys and the fourth set of idler pulleys form an outer pulley layer arranged adjacent to the inner pulley layer.

23. The haptic device of claim 22, further comprising a second proximal motor, coupled to a proximal end of the second linkage member, that drives a third degree of freedom of the second linkage member.

24. The haptic device of claim 23, wherein the end effector includes a distal motor that drives an additional degree of freedom of the haptic device.

25. The drive system of claim 1, wherein the first and second driving pulleys are configured to rotate in a first direction and the first and second idler pulleys are configured to rotate in a second direction opposite the first direction.

26. The drive system of claim 5, wherein the cable comprises a single continuous cable that traverses the forward cable path and the reverse cable path.

27. The drive system of claim 9, wherein the first, second, third, and fourth driving pulleys are substantially equal in diameter.

28. The haptic device of claim 13, wherein the first and second driving pulleys are configured to rotate in a first direction and the first and second idler pulleys are configured to rotate in a second direction opposite the first direction.

29. The haptic device of claim 15, wherein the cable comprises a single continuous cable that traverses the forward cable path and the reverse cable path.

* * * * *